(12) United States Patent
Lin

(10) Patent No.: US 10,591,410 B2
(45) Date of Patent: Mar. 17, 2020

(54) FLEXIBLE MID-INFRARED PHOTONICS FOR CHEMICAL SENSING

(71) Applicant: The Texas A&M University System, College Station, TX (US)

(72) Inventor: Pao Tai Lin, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/179,502

(22) Filed: Nov. 2, 2018

(65) Prior Publication Data

US 2019/0128798 A1    May 2, 2019

Related U.S. Application Data

(60) Provisional application No. 62/580,686, filed on Nov. 2, 2017.

(51) Int. Cl.
*G01N 21/35* (2014.01)
*G01N 21/25* (2006.01)
(Continued)

(52) U.S. Cl.
CPC ........... *G01N 21/255* (2013.01); *G01N 21/35* (2013.01); *G01N 21/3504* (2013.01);
(Continued)

(58) Field of Classification Search
CPC ........ G02B 6/428; G02B 6/43; G02B 6/4214; G02B 23/26; G02B 6/0036; G02B 6/0045; G02B 6/0055; G02B 6/0068; G02B 6/0076; G02B 6/0083; G02B 6/02385; G02B 6/12002; G02B 6/1221; G02B 6/13; G02B 6/14; G02B 6/30; G02B 6/3885; G02B 6/42; G02B 2006/12038; G02B 2006/12069; G02B 2006/12126; G02B 2006/1213; G02B 2006/12183; G02B 21/0076; G02B 21/04; G02B 23/2407; G02B 23/2423; G02B 23/243; G02B 6/0003; G02B 6/0008; G02B 6/001; G02B 6/0018; G02B 6/0023; G02B 6/0028;
(Continued)

(56) References Cited

U.S. PATENT DOCUMENTS 7,559,594 B2    7/2009  Mcmillen
7,724,997 B2 *  5/2010  Kittaka ............... G02B 6/1225
                                                    385/129
(Continued)

OTHER PUBLICATIONS

U.S. Appl. No 16/179,470, filed Nov. 2, 2018, Mid-Infrared Integrated Photonics for Chemical Sensing.
(Continued)

*Primary Examiner* — Michael P Stafira
(74) *Attorney, Agent, or Firm* — Schwegman Lunberg & Woessner, P.A.

(57) ABSTRACT

A flexible waveguide structure including a waveguide on a flexible substrate, both having transparent windows in the mid-infrared range, may serve as a photonic chemical sensor for measuring characteristic absorptions of analytes brought in physical contact with the waveguide. Such a sensor may, in accordance with some embodiments, be formed by an aluminum-nitride waveguide on a borosilicate substrate.

19 Claims, 8 Drawing Sheets

(51) Int. Cl.
*G02B 6/10* (2006.01)
*G01N 21/3577* (2014.01)
*G01N 21/3504* (2014.01)
*G01N 21/77* (2006.01)

(52) U.S. Cl.
CPC ..... *G01N 21/3577* (2013.01); *G01N 21/7703* (2013.01); *G02B 6/102* (2013.01); *G01N 2201/0873* (2013.01)

(58) Field of Classification Search
CPC ...... G02B 6/003; G02B 6/0031; G02B 6/005; G02B 6/0051; G02B 6/0063; G02B 6/0073; G02B 6/02076; G02B 6/0288; G02B 6/036; G02B 6/102; G02B 6/12; G02B 6/12004; G02B 6/122; G02B 6/3624; G02B 6/366; G02B 6/368; G02B 6/3825; G02B 6/3834; G02B 6/3841; G02B 6/3861; G02B 6/3882; G02B 6/3897; G02B 6/4203; G02B 6/4204; G02B 6/4224; G02B 6/4227; G02B 6/4239; G02B 6/4245; G02B 6/4246; G02B 6/425; G02B 6/4253; G02B 6/4255; G02B 6/4259; G02B 6/4274; G02B 6/4281; G02B 6/4284; G02B 6/4295; G02B 6/4416; G02B 6/443; G02B 6/4461; G02B 6/1225; G02B 6/32; G02B 6/4249; G02B 6/4292; G02B 6/0013; G02B 6/0016; G02B 6/02314; G02B 6/4278; G02B 17/002; G02B 17/06; G02B 17/061; G02B 17/0808; G02B 17/086; G02B 1/002; G02B 2006/0098; G02B 2006/12102; G02B 2006/12142; G02B 21/0028; G02B 23/24; G02B 23/2453; G02B 23/2461; G01B 11/005; G01B 11/02; G01B 11/14; G01B 11/22; G01B 11/24; G01B 11/2513; G01B 11/2518; G01B 11/2527; G01B 11/2536; G01J 3/30; G01N 21/255; G01N 21/35; G01N 21/3504; G01N 21/3577; G01N 21/3581; G01N 21/7703; G01N 22/00; G01N 2201/0873
See application file for complete search history.

(56) References Cited

U.S. PATENT DOCUMENTS

| | | | |
|---|---|---|---|
| 9,709,504 | B2* | 7/2017 | Osterlund ............ G01N 21/552 |
| 2006/0228064 | A1 | 10/2006 | Hunt et al. |
| 2009/0041405 | A1* | 2/2009 | Dai .................... G01N 21/4133 385/12 |
| 2011/0090484 | A1 | 4/2011 | Oesterlund et al. |
| 2013/0142477 | A1* | 6/2013 | Diemeer .............. G01N 21/648 385/12 |
| 2014/0185042 | A1 | 7/2014 | Baets et al. |
| 2016/0139335 | A1 | 5/2016 | Abel et al. |
| 2017/0055906 | A1* | 3/2017 | Bremer .............. A61B 5/14532 |
| 2017/0082544 | A1 | 3/2017 | Van Dorpe et al. |
| 2017/0285264 | A1 | 10/2017 | Cote et al. |
| 2019/0129094 | A1 | 5/2019 | Lin |

OTHER PUBLICATIONS

U.S. Appl. No. 16/589,818, filed Oct. 1, 2019, Mid-Infrared Waveguide Sensors for Volatile Organic Compounds.

"U.S. Appl. No. 16/179,470, Non Final Office Action dated Sep. 18, 2019", 11 pgs.

Chen, Li, et al., "12.5 pm/V hybrid silicon and lithium niobate optical microring resonator with integrated electrodes", Optics Express 27003, vol. 21, No. 22, (Nov. 2013), 8 pgs.

Jin, Tiening, et al., "Flexible Mid-infrared Aluminium Nitride Waveguides for Real-time and Label-Free Chemical Sensing", SeTu1E.3. Advanced Photonics Congress (IPR, Networks, NOMA, PS, Sensors, SPPCom) ODS, (2017).

Jin, Tiening, et al., "Monolithic Mid-Infrared Integrated Photonics Using Silicon-on-Epitaxial Barium Titanate Thin Films", ACS Appl. Mater. Interfaces, (2017), 21848-21855.

Jin, Tiening, et al., "Monolithically Integrated Si-on-AlN Mid-Infrared Photonic Chips for Real-Time and Label-Free Chemical Sensing", ACS Appl. Mater. Interfaces, vol. 9, (2017), 42905-42911.

Jin, Tiening, et al., "Real-Time and Label-Free Chemical Sensor-on-a-chip using Monolithic Si-on-BaTiO3 Mid-Infrared waveguides", Scientific Reports 7, (2017), 8 pgs.

Lin, Pao, et al., "Label-Free Glucose Sensing Using Chip-Scale Mid-Infrared Integrated Photonics", Adv. Optical Mater, (2016), 1755-1759.

Lin, Pao, "Real-time and label-free chemical sensing using flexible mid-infrared photonic circuits (Conference Presentation)", Proc. SPIE 10662, Smart Biomedical and Physiological Sensor Technology XV, 106620N, (May 2018), 5 pgs.

Rabiei, Payam, et al., "Heterogeneous lithium niobate photonics on silicon substrates", Optics Express 25573, vol. 21, No. 21, (2013), 9 pgs.

Weigel, Peter, et al., "Lightwave Circuits in Lithium Niobate through Hybrid Waveguides with Silicon Photonics", Scientific Reports, (2016), 9 pgs.

* cited by examiner

FLEXIBLE MID-INFRARED PHOTONICS FOR CHEMICAL SENSING

PRIORITY

This application claims the benefit of priority to U.S. Provisional Application Ser. No. 62/580,686, filed Nov. 2, 2017, which is incorporated by reference herein in its entirety.

TECHNICAL FIELD

The present disclosure relates generally to integrated photonics. More specifically, various embodiments relate to photonics-based chemical or biochemical sensors.

BACKGROUND

Infrared (IR) spectroscopy is routinely used for material identification and characterization. Numerous chemical functional groups have characteristic absorption bands and absorption patterns (called "fingerprints") in the IR spectrum that allow determining, or at least narrowing the possibilities for, the types of molecules present in a sample. A common laboratory instrument used for IR spectroscopy is a Fourier transform infrared (FTIR) spectrometer. F spectrometers are benchtop-size apparatus that generally test one sample at a time; are not easily portable; and, as a result, cannot be easily used in the field. In recent years, therefore, efforts have been made to develop chip-scale photonics-based IR spectrometers and chemical/biochemical sensors, e.g., using standard rigid photonic material platforms, such as silicon (Si) on silicon oxide ($SiO_2$).

In parallel with the development of photonic chemical sensors, flexible photonics has attracted a lot of attention due to its key role in emerging applications such as portable and wearable imaging and display arrays, sensors, and optical interconnects. Both passive and active photonic devices have been successfully integrated on flexible polymer substrates. These polymer substrates, however, are opaque in the mid-IR wavelength range (corresponding to wavelengths greater than 2.5 µm), into which the characteristic absorptions of many chemicals fall. Furthermore, the polymeric substrates decompose and deform under high temperature and degrade when exposed to organic solvents, limiting they applications in harsh environmental conditions. Accordingly, current flexible photonics platforms are unsuited for many chemical sensing applications.

BRIEF DESCRIPTION OF THE DRAWINGS

Various aspects and example embodiments are described herein with reference to the accompanying drawings, in which.

DESCRIPTION

Figure 1A:
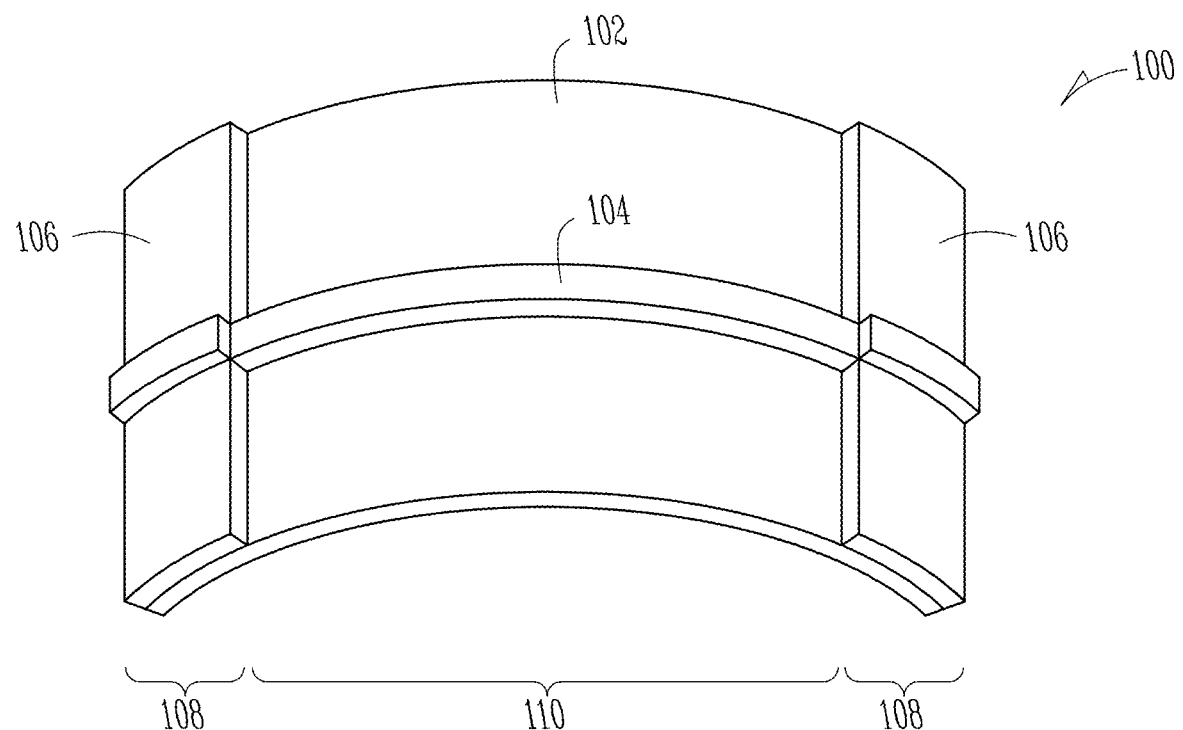
FIGS. 1A and 1B are schematic top and cross-sectional views, respectively, of a flexible waveguide structure in accordance with various embodiments.

Disclosed herein is a material platform for flexible photonics with an operating range extending into the mid-IR regime, suitable for implementing flexible, wearable photonics-based chemical sensors, among other applications. Fabrication methods for making such flexible sensors as well as chemical sensing systems and methods employing them are also described. The term "chemical" is hereinafter used broadly in reference to any organic or inorganic chemical substance, and is intended to encompass, without being limited to, biochemicals, that is, substances occurring within living organisms and/or relating to biological processes. Accordingly, "chemical sensors" and "chemical sensing methods" described herein are also intended to include biochemical sensors and biochemical sensing methods, and, indeed, various embodiments described herein are very suited to biochemical sensing.

In accordance with various embodiments, a flexible waveguide structure including a waveguide on an ultra-thin, bendable substrate is created from materials that have mid-IR-transparent windows, i.e., are transparent to infrared light over a wavelength range including wavelengths greater than 2.5 µm. For example, in some embodiments, the waveguide is made from aluminum nitride (AlN), which has a wide transmission spectrum covering ultraviolet, visible, near-IR, and mid-IR up to about 10 µm, and the substrate is made from borosilicate, which has a transparent window in the near-IR and mid-IR region up to about 3.4 µm. In addition, in some embodiments, a thin intermediate layer that is mid-IR-transparent up to greater wavelengths than the substrate is added as an undercladding between AlN and borosilicate to expand the operation window of the entire device. For example, an undercladding made of magnesium fluoride ($MgF_2$) can achieve an operating wavelength range of the waveguide structure extending to about 8 µm.

Borosilicate is considered rigid (or even brittle) in bulk, but a very thin borosilicate sheet can be moderately bent without cracking, as the surface strain induced by bending is inversely proportional to the template thickness. Accordingly, for flexible photonic structures in accordance herewith, ultra-thin substrates, herein understood as substrates with thicknesses of less than 50 µm are used, in conjunction with waveguides (or other integrated photonic components) and, optionally, undercladdings that are themselves only a few microns thick. In some embodiments, the flexible substrate, or even the integrated photonic structure as whole, has a thickness of less than 30 µm. The flexibility of the structure may be characterized by a bend radius (which is the minimum radius of curvature to which the sheet can be bent without damage) of less than 1 cm. To prevent the waveguide from peeling off when the substrate is bent, the waveguide is, in some embodiments, "anchored" to the substrate at one or both ends by an overlaying top cladding layer, leaving a center section of the waveguide unclad to allow exposure to the external medium.

To use the waveguide as a chemical sensor, the surface of the waveguide is exposed to a sample, and mid-IR light is coupled into the waveguide at one end and detected at the other end. As the light is guided in the waveguide, it remains largely unaffected by the waveguide itself and the substrate or, if applicable, undercladding, due to their mid-IR transparency, but its evanescent field can interact with an analyte (or analytes) within the sample at characteristic absorption wavelengths of the analyte(s), resulting in an absorption spectrum of the detected light that is indicative of the analyte(s). Beneficially, waveguide-based chemical sensors as described herein facilitate monolithic integration of the sensors with other optical components of a larger photonic circuit, such as, e.g., on-chip light sources and detectors.

Apart from mid-IR transparency and flexibility, materials and material combinations in accordance with various embodiments described herein also provide other benefits. For example, AlN has large optical nonlinearities, which renders it suitable for applications of nonlinear light generation (such as second-harmonic generation as well as sum-frequency and difference-frequency generation). The created light from nonlinear light generation can be used for sensing applications as described herein. Borosilicate has thermal and chemical resistance, making it capable of biochemical and toxic sensing under harsh environments. Furthermore, both borosilicate substrates and AlN are both compatible with the complementary metal oxide semiconductor (CMOS) process and various conventional semiconductor materials (such as Si and $SiO_2$), facilitating relatively low-cost and simple manufacturing as well as monolithic integration of various photonic circuit components.

In the following, various aspects and example embodiments of the disclosed subject matter are described with reference to the accompanying drawings.

Figure 1B:
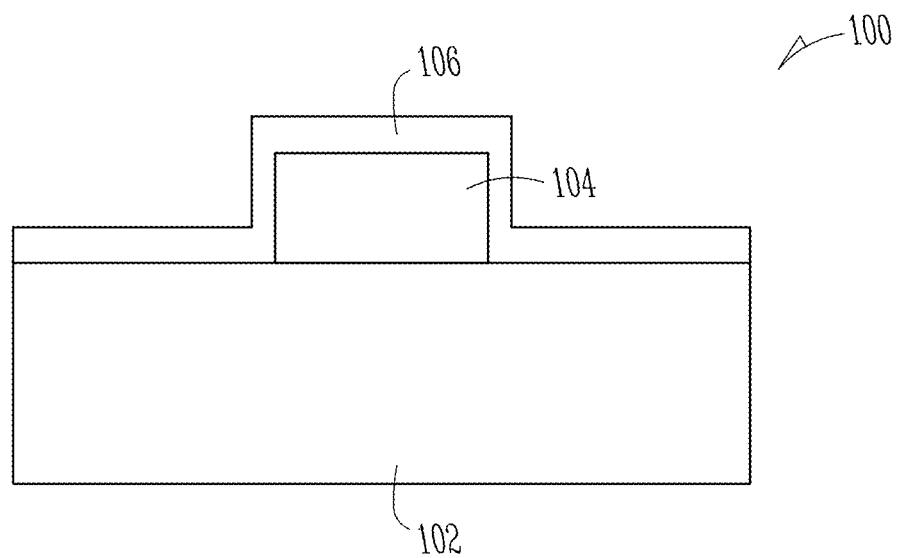

FIGS. 1A and 1B are schematic top and cross-sectional views, respectively, of a flexible waveguide structure 100 in accordance with various embodiments. The waveguide structure 100 includes an ultra-thin substrate 102 and a waveguide 104 formed on top of the substrate 102. As shown, the waveguide 104 may be a strip (or "ridge") waveguide with a rectangular cross-section, but other cross-sectional shapes and waveguide types (e.g., rib waveguides, slab waveguides, etc.) are also possible. To allow bending along with the substrate, the waveguide 104 generally has a thickness (or "height") on the order of microns, e.g., in some embodiments, no more than 4 µm. In one example embodiment, the waveguide 104 is about 2 µm thick and about 10 µm wide. The length of the waveguide is usually significantly greater than its width, e.g., at least 1 mm, or at least 5 mm in some embodiments. The waveguide structure 100 further includes a top cladding 106 that is disposed, e.g., in strips, over end sections 108 of the waveguide 104 and adjacent portions of the substrate 102, leaving a center section 110 of the waveguide exposed. The top cladding 106 serves to firmly anchor the waveguide 104 on the surface of the substrate 102, preventing the waveguide 104 from peeling off as the structure 100 is bent. In some embodiments, the waveguide structure 100 further includes an undercladding (not shown) disposed between the substrate 102 and the waveguide 104.

The waveguide 104 and substrate 102 and/or undercladding are made of materials that are transparent to mid-IR light across a specified, generally application-dependent wavelength range, such that light within that range can propagate along the waveguide substantially unattenuated. A material layer or component is herein deemed "transparent" to light of a given wavelength if it transmits a specified percentage (e.g., at least 80%, or at least 95%) of the light; the percentage may be set based on the needs of the particular application. For instance, in the context of chemical sensing, any absorption of light by the waveguide and substrate and/or undercladding should be negligible to the characteristic absorption of the analyte (i.e., the chemical substance of interest) at relevant analyte concentrations. In various embodiments, the waveguide 104 is made of AlN, aluminum oxynitride (AlON), chalcogenide, halide, or metal oxide, all of which have IR-transparent windows extending beyond 5 µm (with halides and chalcogenides even extending into the far-IR regime) and are, moreover, optically nonlinear. Alternatively, the waveguide 104 may be made of a Group-IV semiconductor material such as silicon, germanium, silicon nitride (all being transparent up to about 8 µm or more), or silica (which extends into the mid-IR regime beyond 3 µm). The substrate 102 may be made of borosilicate, which is IR-transparent up to about 3.4 µm. The optional undercladding may be made, e.g., of $MgF_2$, which is IR-transparent up to at least 8 µm; it may be used on top of the borosilicate substrate to avoid evanescent light from being absorbed at wavelengths beyond 3.4 µm. The combination of waveguide and substrate materials may be selected such that the refractive index of the waveguide substantially exceeds that of the substrate (e.g., by a refractive-index of at least 0.3) over the intended operating range of the structure 100 to ensure sufficient confinement of an optical mode in the waveguide 104. In one embodiment, the waveguide structure 100 is implemented using an AlN waveguide 104 on a borosilicate substrate 102. The top cladding 106 may be made, for instance, of $SiO_2$, aluminum oxide, $MgF_2$, or barium fluoride ($BaF_2$).

Figure 2:
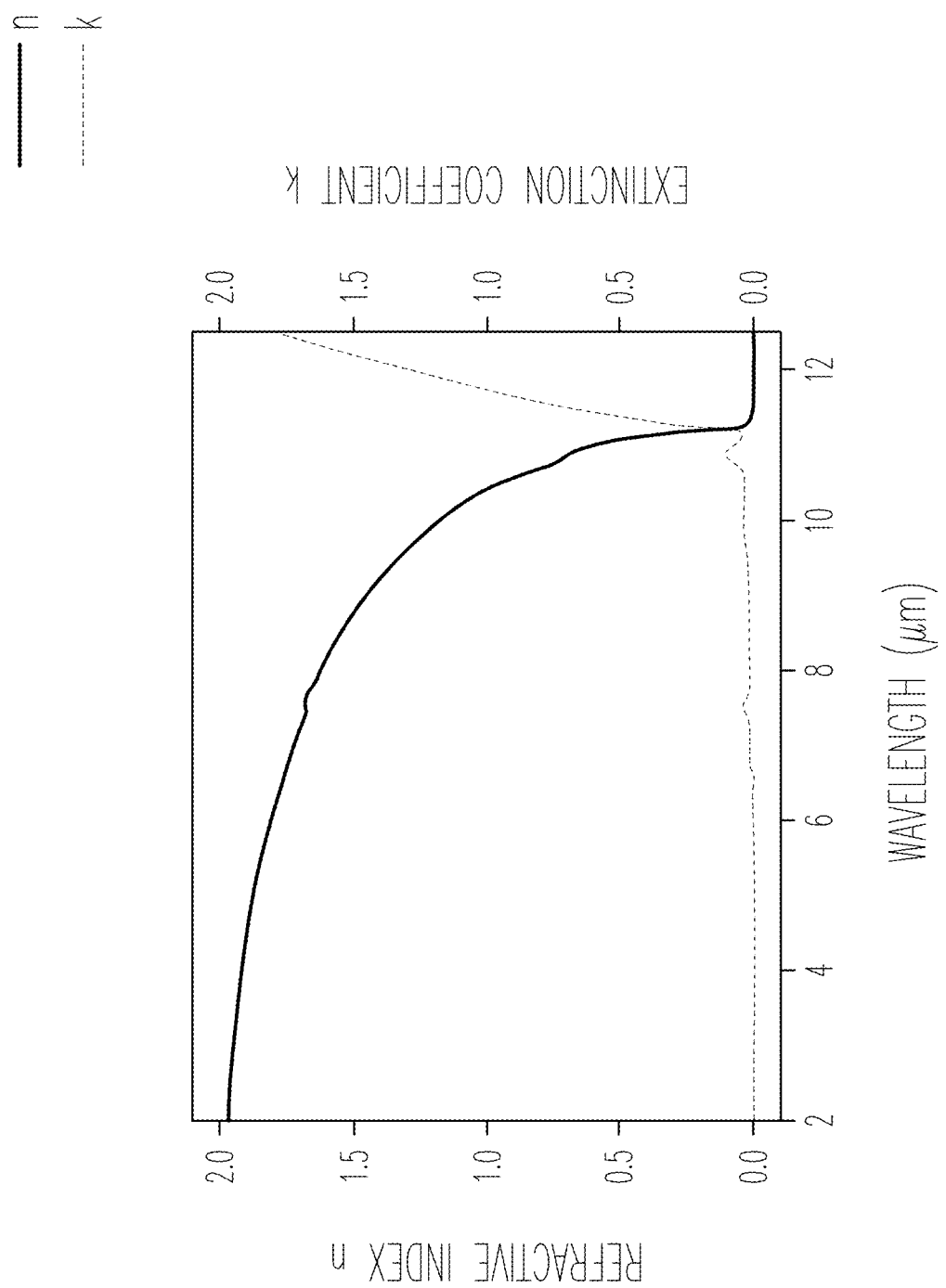
FIG. 2 is a graph of the wavelength-dependent refractive index and extinction coefficient of an aluminum nitride thin film as may be used as a waveguide material in accordance with various embodiments.

FIG. 2 is a graph of the wavelength-dependent refractive index n and extinction coefficient k (also known as the imaginary refractive index) of a deposited AlN thin film as may be used as a waveguide material in accordance with various embodiments, measured over a wavelength range from 2 µm to 13 µm using IR-variable angle spectroscopic ellipsometry (IR-VASE). As shown, the refractive index n decreases slowly from 1.9 at 2 µm to 1.6 at 9 µm until a strong dispersion is found after 10 µm. The small variation of n over a broad mid-IR spectral range offers low optical dispersion, as is beneficial for various applications, including efficient nonlinear light generation and accurate chip-scale chemical sensing. The relative low extinction coefficient k observed before 10 µm is likewise beneficial, as it bears the potential for broadband mid-IR photonic circuits.

Figures 3A, 3B:
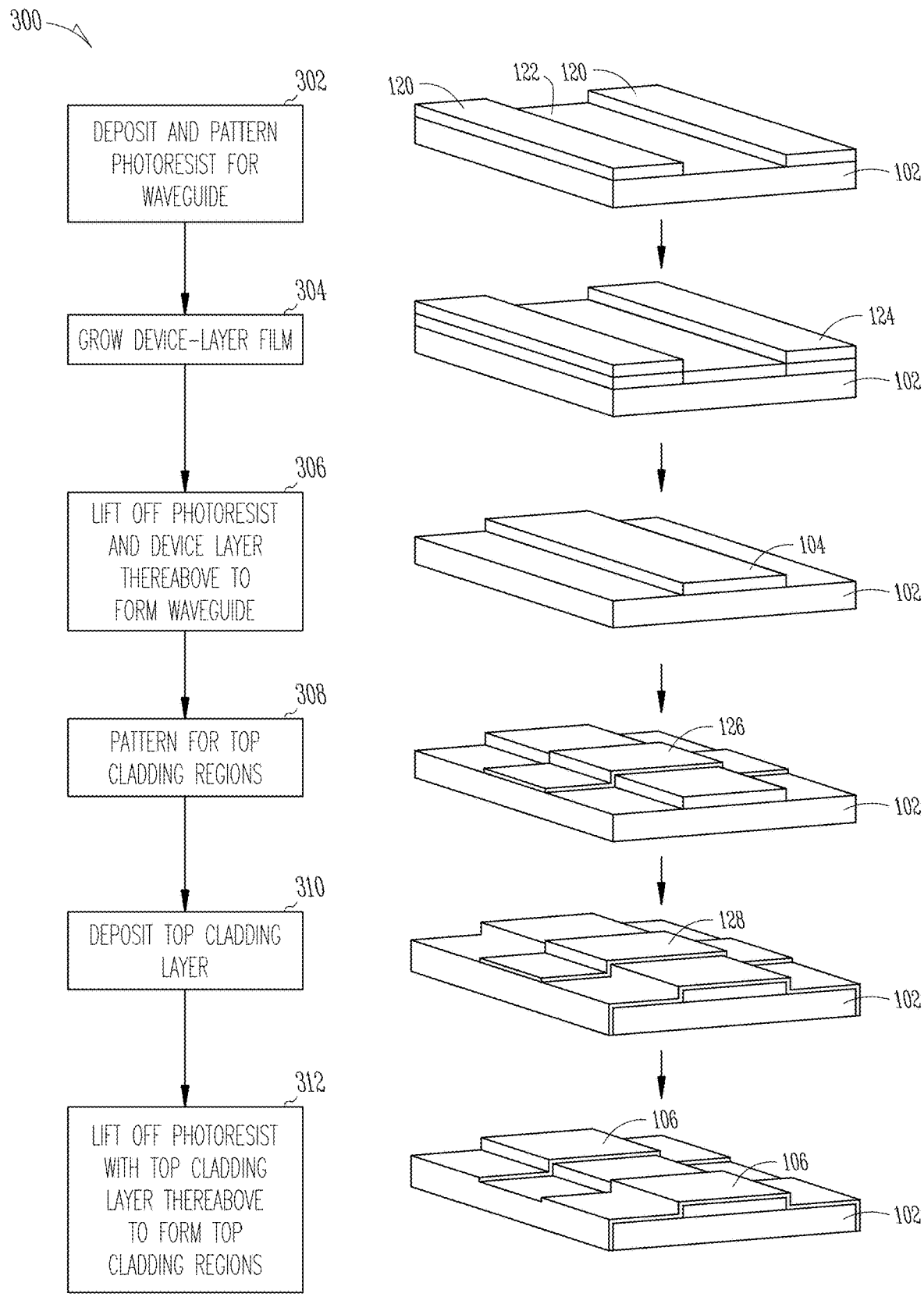
FIG. 3A is a flow chart illustrating a method of fabricating the device structure of FIG. 1 in accordance with various embodiments.
FIG. 3B is a sequence of diagrams illustrating the structures resulting from the various steps shown in FIG. 3A.

Turning now to FIGS. 3A and 3B, an example method 300 of fabricating the waveguide structure 100 in accordance with various embodiments is shown with a flow chart of the process steps (FIG. 3A) side by side with the respective structure resulting at the end of each step for an example AlN-on-borosilicate implementation (FIG. 3B). The method 300 involves thin-film deposition and standard CMOS processing steps, including photolithographic patterning and lift-off, to create both the waveguide 104 and the top cladding 106. In more detail, starting from a thin sheet (e.g., of borosilicate) serving as the substrate 102 (which may, optionally, have a thin undercladding disposed thereon), a photoresist layer 120 is first deposited and photolithographically patterned to expose only a region 122 of the substrate surface on which the waveguide 104 is to be formed (step 302). A thin device-layer film 124 is then grown on the patterned substrate 102 (step 304), e.g., by chemical vapor deposition (CVD), molecular beam epitaxy (MBE), or sputtering. For example, in one embodiment, a thin (e.g., one to a few microns thick) AlN film is deposited by room-temperature DC sputtering. In a subsequent lift-off step 306, the photoresist 120 and device-layer material 124 disposed thereabove are removed, leaving only the waveguide 104 on the substrate 102. To form the top cladding 106, another photoresist layer 126 is deposited and photolithographically patterned, this time covering the center section of the waveguide 104 and adjacent substrate portions and exposing only the end sections of the waveguide and adjacent substrate portions where the top-cladding strips are to be created (step 308). A thin cladding layer 128, e.g., of $SiO_2$, is then deposited over the entire surface (step 310), followed by lift-off of the photoresist 126 and cladding material thereabove (step 312), which results in the final waveguide structure with a waveguide 104 pinned to the substrate 106 by strips of top cladding 106.

Using the above-described fabrication method, high-quality monolithically integrated (referring to the thin-film deposition used to create them) AlN-on-borosilicate waveguide structures can be achieved. It has been experimentally verified, for example, that the AlN waveguides firmly adhere to the borosilicate substrate and are able to tolerate high mechanical stress. Further, the AlN waveguide has been shown to possess a well-defined ridge structure without bends or distortions found on the edge, nor cracks or indents on the surface. The sharp waveguide edges reduce waveguide propagation loss caused by light scattering, enabling accurate waveguide sensing. In addition, the interface between the top AlN waveguide and borosilicate substrate (which simultaneously serves as an undercladding) is well-resolved. By preparing the AlN waveguides using the lift-off process rather that an aggressive etching process, depletion damage on the device surfaces or interfaces can be avoided.

Figure 4A:
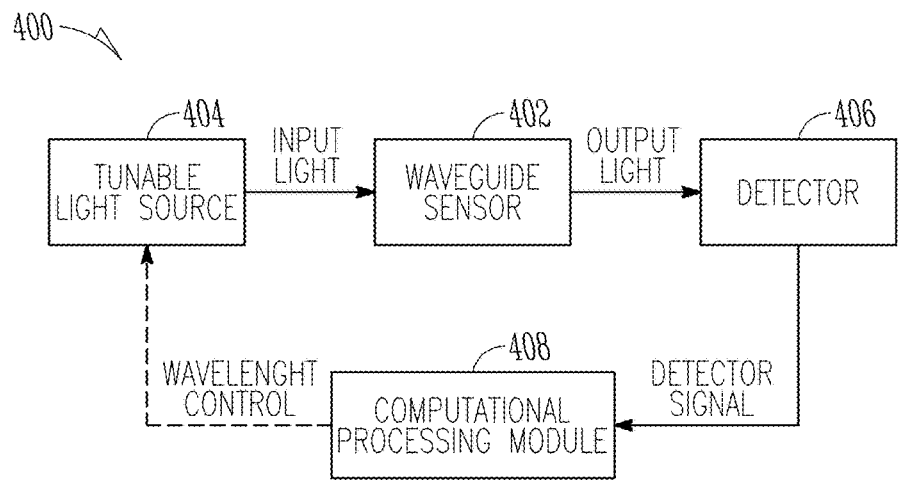
FIGS. 4A and 4B are block diagrams form of chemical sensing systems incorporating the waveguide structure of FIG. 1 in accordance with various embodiments.
Figure 4B:
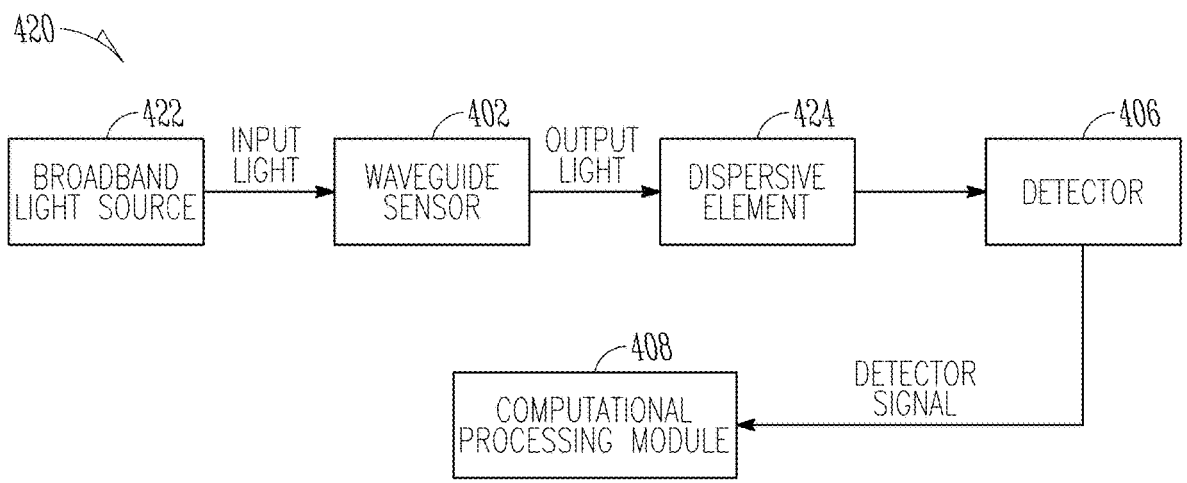

Flexible waveguide structures 100 with mid-IR-transparent windows as described herein can be used as chemical sensors. FIGS. 4A and 4B provide, in block-diagram form, conceptual depictions of example chemical sensing systems in accordance with various embodiments that each incorporate such a waveguide sensor (as implemented by a waveguide structure 100). Shown in FIG. 4A is a system 400 that includes, in addition to the waveguide sensor 402, a tunable mid-IR light source 404 (e.g., a tunable laser) coupling light, directly or indirectly, into the waveguide sensor 402, a mid-IR detector 406 measuring the light exiting the waveguide sensor 402, and a computational processing module 408 that processes the measured signal. The computational processing module 408 may be implemented in analog or digital circuitry; if the latter, the electronic output of the detector 406 may be converted into a digital signal by an analog-to-digital converter (not shown). In some embodiments, the computational processing module 408 is provided by a programmable processor (e.g., a field-programmable gate array (FPGA) or general-purpose central processing unit (CPU)) executing suitable software).

The light source 404 is tunable over an operating wavelength range of the sensing system 400, facilitating measurements of absorption spectra, across that wavelength range, of samples in contact with the waveguide sensor 402 and detection of analytes with characteristic absorptions at wavelengths within that range. In some embodiments, the operating wavelength range extends from about 2.5 µm or less to about 3.4 µm or more, including the characteristic absorptions of, e.g., the —CH, —OH, and —NH functional groups. The detector 406 may be, for instance, a photodetector that measures the overall intensity of the light output by the waveguide sensor 402, or, alternatively, a camera (e.g., an array of photosensors) that allows imaging the optical mode at the waveguide sensor output. Either way, the detector 406 is selected or configured to be sensitive to light within the operating wavelength range. In various embodiments, for instance, an indium antimonide (InSb) infrared camera, which is responsive to light from less than 1 µm up to 5.3 µm, or an HgCdTe (MCT) camera, which is sensitive up to at least 7 µm, is used. The computational processing module 408 may be configured to create a spectrum by associating the measured output signal of the sensor 402 at a given time with the respective wavelength input by the light source at that time. The computational processing module 408 may have knowledge of the light-source wavelength by virtue of controlling the tunable wavelength itself, or by receiving a signal indicative of the wavelength from a separate light-source controller (not shown). In addition to computing a spectrum, the computational processing module 408 may also implement processing logic for analyzing the spectrum, e.g., based on data about the absorption characteristics of a various chemical substances (e.g., as stored in memory of the computational processing module 408), to identify analytes present within the sample and/or determine their concentration. Alternatively to acquiring a spectrum by varying the wavelength with time, the system 400 can also be operated continuously at a given wavelength, e.g., corresponding to the characteristic absorption of a certain analyte, to measure a time-resolved absorption signal indicative of a (possibly variable) concentration of the analyte in the sample.

FIG. 4B shows an alternative sensing system 420 including, instead of a tunable light source, a light source 422 providing broadband light covering the operating wavelength range. To facilitate the acquisition of a spectrum, the system 400 may further include a dispersive element 424 at the output of the waveguide sensor 402, preceding the detector(s) 406, to spatially spread out the light by wavelength. Using a camera as the detector 406; the output intensity at different wavelengths can then be measured at different respective locations within the sensor array of the camera. Alternatively to a camera, multiple photodetectors (e.g., a photodiode array detector) may be placed at different locations corresponding to different respective wavelengths, or a single detector (or camera) may be moved to measure the intensity for different wavelengths. In a broadband-light sensing system 420, the computational processing module 408 generates a spectrum by associating the location of the measured light intensity with wavelength.

In both sensing systems 400, 420, the light emitted by the light source 404, 422 may be collimated, e.g., with a refractive lens, into an optical fiber, which may then be butt-coupled to the waveguide sensor 402. Similarly, the light output by the waveguide sensor 402 may be focused by a lens (e.g., a barium fluoride biconvex lens) onto the camera or other detector 406. Alternatively, the light source 404, 422 and/or detector 406 may be implemented as photonic-circuit components and monolithically integrated with the sensor 402 on the same substrate. Lasers and detectors may be formed, e.g., by device structures created either in the AlN layer along with the waveguide sensor 402 or by similar methods in another (e.g., silicon) device layer in conjunction III-V structures serving as active regions and associated electrodes, which may likewise be patterned using standard CMOS processes. Suitable photonic-component structures and manners of manufacturing same are well-known to those of ordinary skill in the art. To provide just one example, in some embodiments, a quantum cascade laser, which can emit light in the mid-IR regime, may be used as the light source. If integrated as photonic-circuit components, the light source 404, 422 and detector 406 may directly couple to a waveguide a portion of which serves as the waveguide sensor 402. In various embodiments, all photonic components of the chemical sensing system can, in this manner, be integrated on a single flexible photonic chip.

Figure 5:
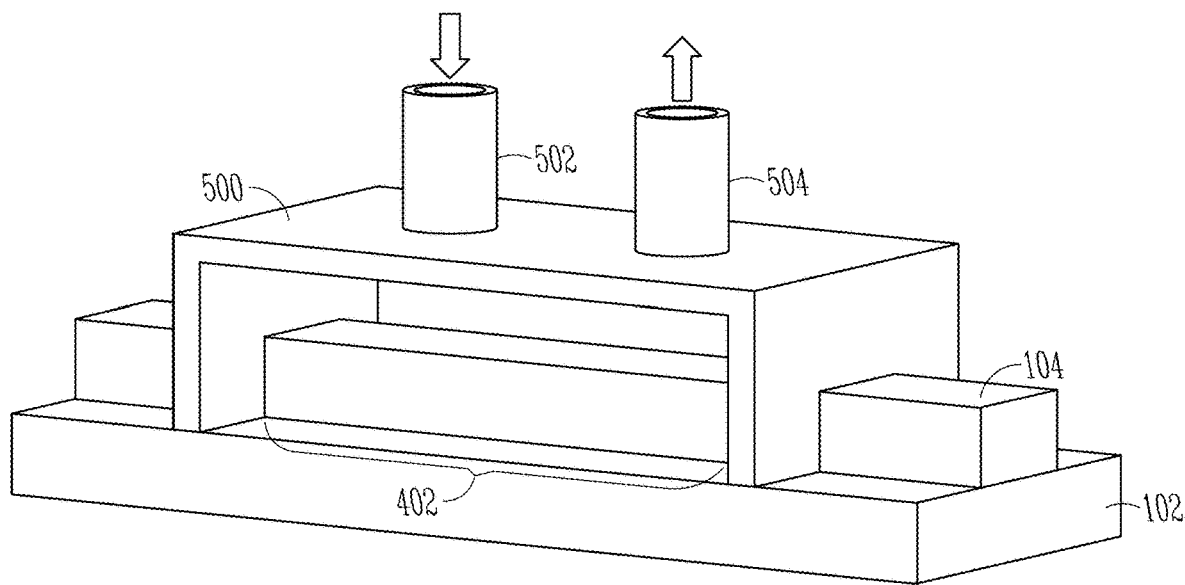
FIG. 5 is a cut-away perspective view of a waveguide sensor enclosed in a microfluid chamber in accordance with various embodiments.

To measure the mid-IR absorptions of a chemical sample, the sample, which may be a liquid, gas, or solid (e.g., powder), can be brought in contact with the exposed center section of the waveguide sensor 402 by various means. For example, a liquid sample may be dispensed onto the waveguide using a pipette, syringe, or similar tool, e.g., to form a drop on top of the waveguide or surrounding a portion of the top and side facets of the waveguide ridge or otherwise wet the waveguide surface. Alternatively, as shown in a cut-away perspective view in FIG. 5, a portion of the waveguide may be enclosed in a microfluidic chamber 500 having a fluid inlet 502 and fluid outlet 504, and the sample may be pumped into and fill that chamber 500. The chamber 500 material and dimensions may be chosen such that the addition of the chamber 500 does not undermine the flexibility of the structure as a whole. In some embodiments, the chamber is formed of a polymeric organosilicon such as polydimethylsiloxane (PDMS), but other materials can also be used. Methods for fabricating such opto-fluidic chips are known to those of ordinary skill in the art.

In various embodiments, multiple waveguide sensors 502 are created on a single chip, e.g., in an array, and optionally each provided with a microfluidic chamber 500 holding the sample, to enable simultaneous measurements of multiple samples for high-throughput applications. The waveguide sensors 402 may receive input light from separate respective (e.g., on-chip) light sources 404, or from a single light source 404 whose output is optically split between multiple channels including the multiple respective sensors 402. Each sensor 402 may have its own respective associated detector 406. It is also possible to switch the output of a light source 404, and similarly the input of a detector 406, cyclically between multiple respective sensors 402 for sequential measurements with the sensors 402; the time in between successive measurements with any given sensor can be used to load a new sample into the associated microfluidic chamber 500, or otherwise bring a new sample into contact with the sensor 402.

Figure 6:
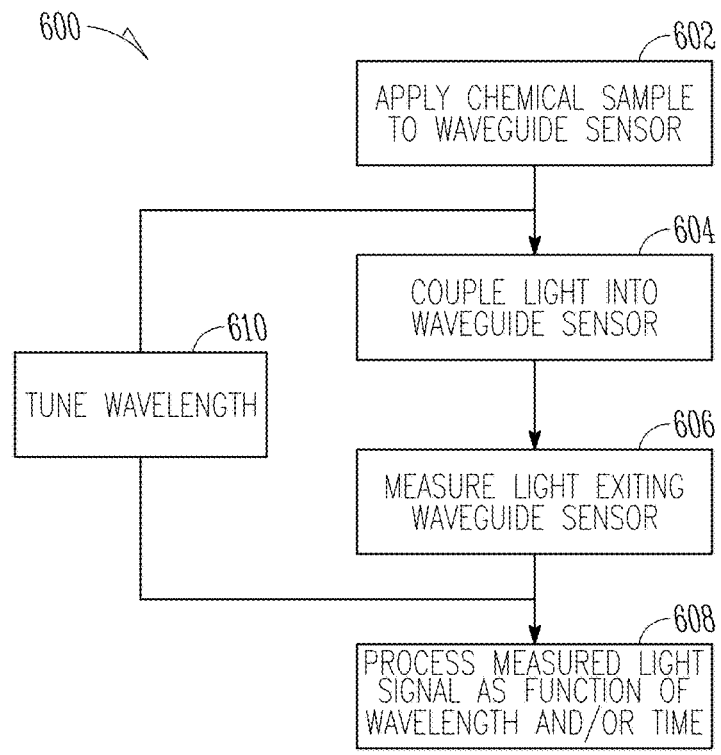
FIG. 6 is a flow chart of a method for chemical sensing in accordance with various embodiments.

With reference now to FIG. 6, a chemical sensing method 600 in accordance with various embodiments is illustrated in the form of a flow chart. The method 600 involves applying a chemical sample to the exposed section of a waveguide sensor 402 as described herein, e.g., by dispensing a sample liquid or powder from above onto the waveguide sensor 402, filling a chamber formed above the waveguide sensor 402 with the sample, and/or flowing a liquid or gas across the surface of the waveguide sensor 402 (e.g., through a chamber formed above the waveguide) (act 602). Once applied to the waveguide sensor 402, the sample can optically interact with the evanescent field extending from the waveguide sensor 402 into the sample, which may result in characteristic absorptions at certain wavelengths. To measure these characteristic absorptions, light is coupled (e.g., from a laser light source) into the waveguide sensor 402 at one end (act 604) and light exiting the waveguide sensor 402 at the other end is measured, e.g., with a camera or photodetector (act 606). In some embodiments, the intensity of the output light is measured with a single photodetector. In other embodiments, the measurement involves capturing an optical mode profile of the output light on camera, and determining an associated mode intensity, which may be, e.g., an aggregate intensity across the profile or a peak intensity (e.g., as aggregated over a small area surrounding the geometric center of the mode profile). The optical mode launched into the waveguide sensor 602 may be a fundamental mode, and may in principle be either transverse electric (TE) or transverse magnetic (TM). In certain embodiments, a TM mode is selectively excited in the waveguide, e.g., by virtue of the waveguide geometry and/or the light source. Beneficially TM modes have been found to exhibit stronger evanescent fields, resulting in stronger interactions of the light with the surrounding chemical sample and, consequently, larger absorption signals.

The measured light (i.e., the generated detector signal) is processed, in act 608, to detect characteristic absorptions therein. To discriminate between multiple possible analytes, the wavelength of the light coupled into the waveguide sensor 402 may be tuned across at least a portion of the operating range of the sensing system (act 610), allowing the processed detector signal to measure the light intensity at the sensor output as a function of wavelength. Observed decreases in intensity at certain wavelengths or within certain wavelength bands correspond to characteristic absorptions that provide information about the analytes. Certain chemical functional groups, such as O—H, N—H, C—H, or groups with double or triple bonds between C, N, and O, for instance, can be identified, and discriminated between, based on their absorption at certain respective wavelengths. For example, —CH absorbs strongly between 3.0 and 3.2 µm, whereas —OH absorbs between 2.8 and 2.9 µm. Further, at longer mid-IR wavelengths (e.g., at wavelengths greater than 6 µm), absorptions due to stretching and bending vibrations (e.g., of C—C, C—O, or C—N bonds) tend to vary with the larger molecular structure. For certain complex (e.g., biological) molecules with multiple stretching and bending absorptions, the absorptions can collectively provide a molecular "fingerprint" that allows identifying the substance. Examples of substances that have absorptions in the mid-IR wavelength range are hexane (absorptive at 6.9 mm) and nitric oxide (absorptive at 5.3 µm). Processing the measured signal may involve, in some embodiments, comparing detected absorptions against the known characteristic absorptions of various chemicals substances to identify which substances are present in the sample. Alternatively or additionally, given knowledge of a certain analyte in the sample and of its respective absorption wavelength, the concentration of that analyte can be monitored by tuning to the respective wavelength, measuring the output intensity as a function of time, and then computationally converting the intensity to concentration (e.g., based on a preceding calibration). Beneficially, the sensing method 600 allows for the label-free detection of analytes, as well as for real-time, in-situ concentration monitoring.

Figure 7A:
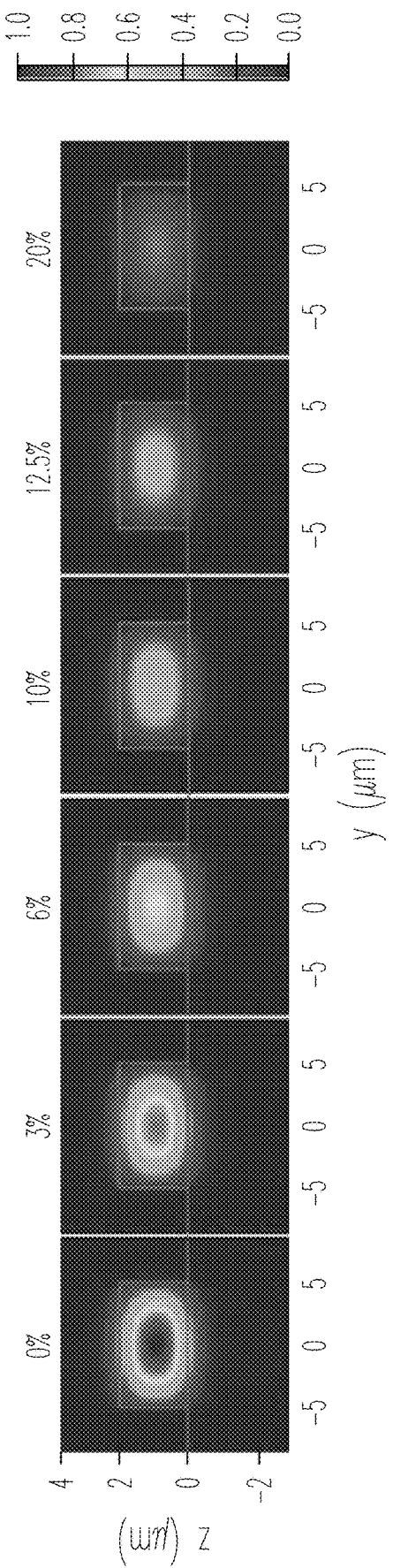
FIG. 7A is a sequence of optical mode profiles in a waveguide structure in accordance with various embodiments for various concentrations of a mid-infrared-absorptive analyte.
Figure 7B:
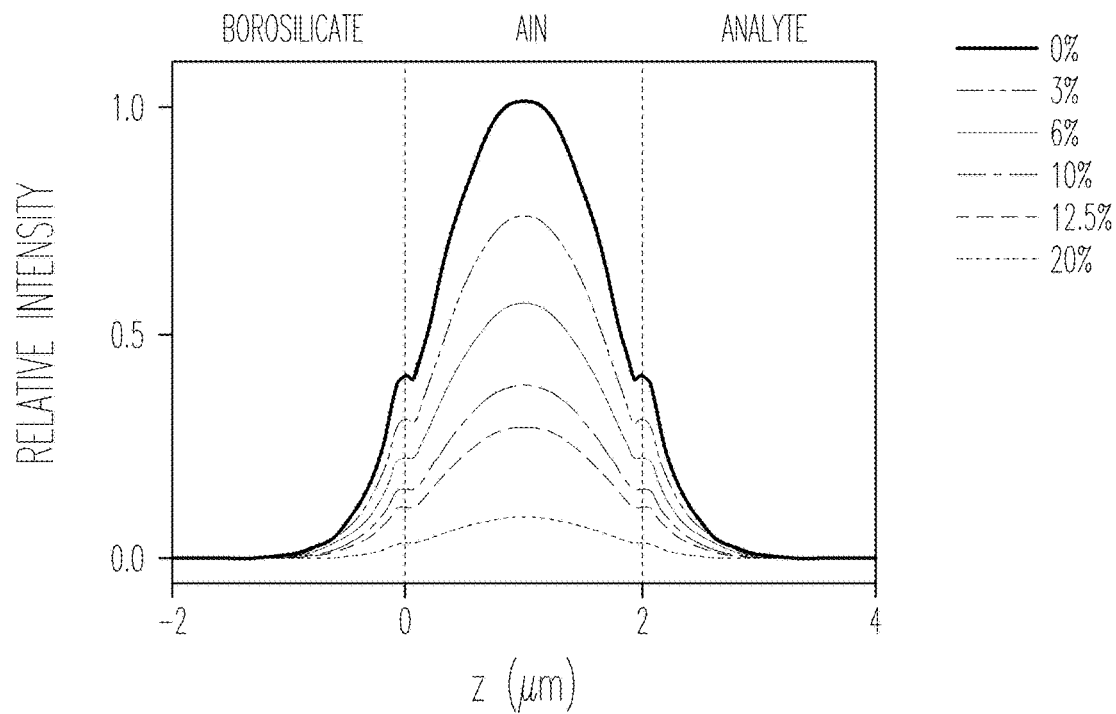
FIG. 7B is a graph showing intensity profiles of the optical mode profiles of FIG. 7A.
Figure 7C:
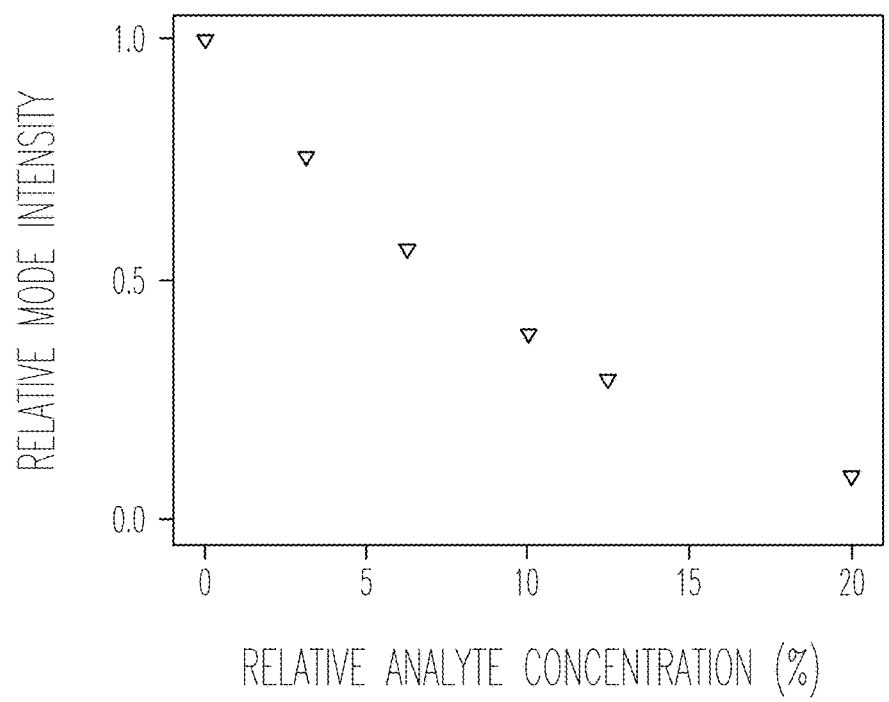
FIG. 7C is a graph showing the mode intensity as a function of concentration of the mid-infrared-absorptive analyte.
Figure 8:
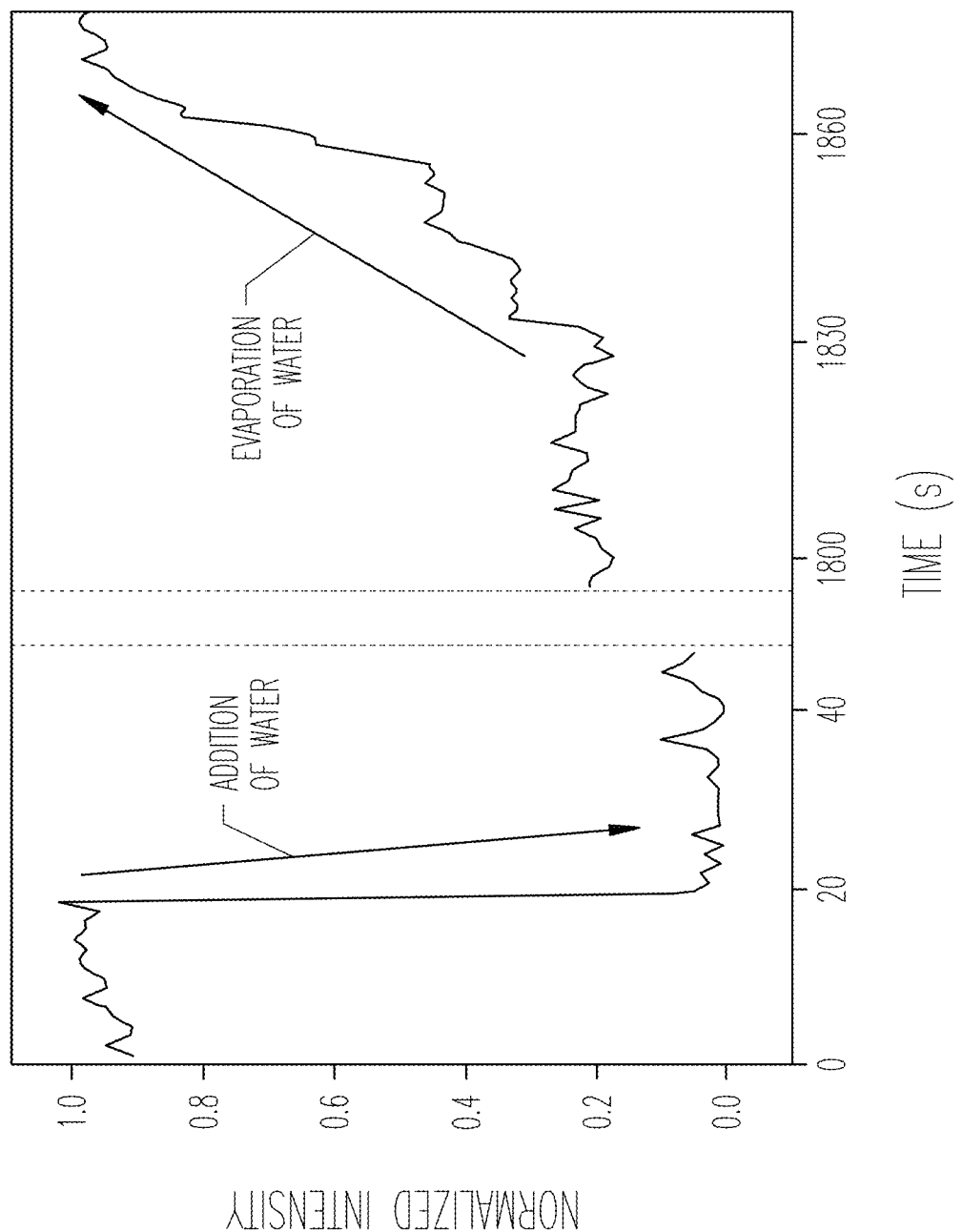
FIG. 8 is a graph illustrating the transient response of a waveguide sensor in accordance with various embodiments to water.

FIGS. 7A-8 illustrate the feasibility of identifying analytes in and/or determining the chemical composition of chemical samples with various examples.

FIG. 7A shows a sequence of optical mode profiles, as computed using the two-dimensional finite element method, in an AlN-on-borosilicate waveguide structure in accordance with various embodiments for various concentrations of a mid-infrared-absorptive analyte. The underlying numerical model assumes a wavelength of the light source of 2.65 µm (corresponding to the O—H absorption), TM polarization of the light, an AlN waveguide 2 µm high and 10 µm wide, and refractive indices of AlN and borosilicate of 1.97 and 1.46, respectively. The extinction coefficient k of the analyte is deemed proportional to the chemical concentration. As shown, a fundamental optical mode with ellipsoid intensity distribution is found inside the AlN waveguide, and its evanescent field extends into both the surrounding chemicals (at z>2 µm) and the borosilicate layer (z<0 µm). The waveguide mode fades quickly as the chemical concentration increases because the evanescent wave is considerably absorbed by the analyte in the vicinity of the waveguide.

FIG. 7B is a graph showing intensity profiles as a function of z (the direction normal to the sensor surface) of the optical mode profiles of FIG. 7A corresponding to the various analyte concentrations. As can be seen, the intensities of the guided wave (0<z<2 µm) and the evanescent wave (z>2 µm and z<0 µm) both decreases drastically when the concentration of the absorptive chemical increases. Yet, the waveguide mode remains the fundamental mode regardless of the concentration. The invariance of the mode profile is beneficial for achieving accurate waveguide sensing, since an excitation of higher order modes would alter the mode profile and also vary the evanescent field, which may lead to false signals during the measurements.

FIG. 7C is a graph showing the mode intensity as a function of concentration of the mid-infrared-absorptive analyte waveguide mode intensity when the analyte concentration gradually increases from 0% to 20%. As can be seen, the mode intensity decreases monotonically with increasing chemical concentration, indicating that the mid-IR waveguide is capable of performing accurate concentration analysis by measuring the attenuation of the waveguide mode intensity.

FIG. 8 is a graph illustrating the transient response of a waveguide sensor in accordance with various embodiments to water, demonstrating real-time chemical detection. The graph shows the measured mode intensity at 2.65 µm, which aligns with the water absorption band, as a function of time t. Before t=20 s, the mode intensity is strong due to the absence of the analyte. Upon wetting the waveguide surface with water at t=20 s, the intensity decreased instantaneously, and the mode disappears because the light is fully absorbed by the water covering the waveguide surface. After t=1830 s, the light intensity gradually recovers as the water evaporates, ultimately reaching its original level once no more water molecules remain on the waveguide surface. This time-resolved characterization demonstrates that the mid-IR waveguide sensor is suitable for in-situ and label-free monitoring of chemical species. In addition, it is not only capable of accurate sensing, but it is also reusable.

Although embodiments have been described with reference to specific example embodiments, it will be evident that various modifications and changes may be made to these embodiments without departing from the broader scope of the invention. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. A mid-infrared photonic chemical sensing system comprising:
a flexible waveguide structure comprising:
an ultra-thin borosilicate substrate;
a waveguide disposed on the ultra-thin borosilicate substrate, the waveguide having, along its length, an exposed center section between two end sections; and
strips of a top cladding deposited over the end sections of the waveguide and adjacent surface regions of the ultra-thin borosilicate substrate, the top cladding anchoring the waveguide on the ultra-thin borosilicate substrate to prevent the waveguide from peeling off the ultra-thin borosilicate substrate when the substrate is bent, the top cladding leaving the center section unclad to expose the center section to an analyte during sensing,
wherein the ultra-thin borosilicate substrate and the waveguide are both transparent to infrared light over an operating wavelength range including wavelengths greater than 2.5 µm.

2. The chemical sensing system of claim 1, wherein the waveguide is made substantially of aluminum nitride or aluminum oxynitride.

3. The chemical sensing system of claim 1, wherein the substrate has a thickness of less than 30 µm.

4. The chemical sensing system of claim 1, wherein the flexible waveguide structure has a bend radius of less than 1 cm.

5. The chemical sensing system of claim 1, wherein the substrate is transparent to mid-infrared light over a wavelength range extending to wavelengths of at least about 3.4 µm.

6. The chemical sensing system of claim 1, wherein the waveguide is transparent to mid-infrared light over a wavelength range extending to wavelengths of at least about 8 µm.

7. The chemical sensing system of claim 1, wherein the waveguide is made from an optically nonlinear material.

8. The chemical sensing system of claim 1, wherein a refractive index of the waveguide exceeds a refractive index of the substrate over the operating wavelength range.

9. The chemical sensing system of claim 1, further comprising:
a light source for coupling light into the waveguide at a first end thereof; and
a detector for measuring light exiting the waveguide at a second end thereof.

10. The chemical sensing system of claim 9, further comprising:
a computational processing module configured to process a signal received from the detector to determine spectral properties of the light exiting the waveguide and measured at the detector and, based thereon, detect one or more analytes in the chemical sample.

11. The chemical sensing system of claim 9, further comprising a microfluidic chamber enclosing the exposed section of the waveguide.

12. The chemical sensing system of claim 9, wherein at least one of the light source or the detector are monolithically integrated with the waveguide on the substrate.

13. A chemical sensing method comprising:
applying a chemical sample to an exposed section of a waveguide sensor formed on a flexible ultra-thin borosilicate substrate, the waveguide sensor and ultra-thin borosilicate substrate both being transparent to light over an operating wavelength range, the operating wavelength range comprising a range from about 2.5 µm to about 3.4 µm, the waveguide sensor being prevented from peeling off the ultra-thin borosilicate substrate when the substrate is bent by strips of a top cladding deposited over end sections of the waveguide sensor and adjacent surface regions of the ultra-thin borosilicate substrate, the exposed section being located between the end sections, the strips of top cladding leaving the exposed section unclad;

coupling light into the waveguide sensor at a first end thereof;

measuring light exiting the waveguide sensor at a second end thereof at a detector; and detecting one or more analytes comprised in the chemical sample based on detection, in the light existing the waveguide sensor at the second end and measured at the detector, of one or more characteristic absorptions at one or more respective wavelengths within the operating wavelength range.

14. The method of claim 13, wherein a wavelength of the light coupled into the waveguide sensor is tuned across at least a portion of the operating wavelength range, and wherein the one or more characteristic absorptions each correspond to a decrease in intensity of the measured light at the respective wavelength.

15. The method of claim 13, further comprising:

monitoring a concentration of one of the one or more analytes based on an intensity of light measured at the respective wavelength of the respective characteristic absorption.

16. The method of claim 13, wherein measuring the light exiting the waveguide sensor comprises measuring an optical mode profile of the light and determining an associated mode intensity.

17. The method of claim 13, wherein detecting one or more analytes comprises determining a composition of a sample comprising at least two compounds selected from the group consisting of water, ethanol, and methanol.

18. The method of claim 13, wherein the one or more analytes comprise a biochemical substance.

19. A method of manufacturing a flexible waveguide structure transparent to infrared light over a wavelength range extending to wavelengths greater than 2.5 µm, the method comprising:

creating a waveguide on top of an ultra-thin borosilicate substrate from a sputtered aluminum nitride film by a complementary metal oxide semiconductor process; and depositing strips of a top cladding over end sections of the waveguide and adjacent surface regions of the ultra-thin borosilicate substrate, the top cladding anchoring the waveguide on the ultra-thin borosilicate substrate to prevent the waveguide from peeling off the ultra-thin borosilicate substrate when the ultra-thin borosilicate substrate is bent, the top cladding leaving a center section of the waveguide between the end sections unclad to expose the center section to an analyte during sensing.

* * * * *